United States Patent [19]

Kozikowski et al.

[11] Patent Number: 5,210,263
[45] Date of Patent: May 11, 1993

[54] INOSITOL PHOSPHATE ANALOGS AND METHODS FOR THEIR USE

[75] Inventors: Alan P. Kozikowski, Ponte Verda Beach, Fla.; Garth Powis, Tucson, Ariz.

[73] Assignees: University of Pittsburgh, Pittsburgh, Pa.; Mayo Foundation For Medical Education and Research, Rochester, Minn.

[21] Appl. No.: 524,267

[22] Filed: May 15, 1990

[51] Int. Cl.$^5$ .............................................. C07F 9/117
[52] U.S. Cl. .................................. 558/161; 558/190; 558/192; 558/194
[58] Field of Search ................ 558/161, 194, 192, 190

[56] References Cited

PUBLICATIONS

Kozikowski, A. P. et al. *J. Chem. Soc. Chem. Commun.* 1988, 1301–1303.
Kozikowski, A. P. et al. *Tetrahedron Lett.* 1989, 30(26), 3365–3368.

Primary Examiner—Mary C. Lee
Assistant Examiner—Michael G. Ambrose
Attorney, Agent, or Firm—Pennie & Edmonds

[57] ABSTRACT

The present invention provides novel inositol phosphate analogs and a method for their use for detecting the phosphatidylinositol cycle-dependent calcium of a cell.

5 Claims, No Drawings

INOSITOL PHOSPHATE ANALOGS AND METHODS FOR THEIR USE

TABLE OF CONTENTS

1. Technical Field
2. Background of the Invention
3. Summary of the Invention
4. Detailed Description of the Invention
4.1 The Method of the Invention
5. Example

1. TECHNICAL FIELD

The present invention provides novel inositol phosphate analogs and a method for their use for detecting the phosphatidylinositol cycle-dependent calcium of a cell.

2. BACKGROUND OF THE INVENTION

For a cell to survive, it must be able to respond rapidly to changes in its environment. Furthermore, for cells to reproduce and carry out other co-operative functions, they must be able to communicate efficiently with each other. Cells most frequently adapt to their environment and communicate with one another by means of chemical signals. An important feature of these signaling mechanisms is that in almost all cases a cell is able to detect a chemical signal without it being necessary for the chemical messenger itself to enter the cell. This permits the cell to maintain tight control of its internal milieu, thereby permitting the cell to respond to its environment without being destroyed by it.

These sensing functions are carried out by a variety of receptors, which are dispersed on the outer surface of the cell and function as molecular antennae. These receptors detect an incoming messenger and activate a signal pathway that ultimately regulates a cellar process such as secretion, contraction, metabolism or growth. The major barrier to the flow of information is the cell's cellular plasma membrane, where transduction mechanisms translate external signals into internal signals, which are then carried throughout the interior of the cell by "second messengers."

In molecular terms, the process depends on a series of proteins within the cellular plasma membrane, each of which transmits information by inducing a conformational change—an alteration in shape therefore, in function—in the protein next in line. At some point the information is assigned to small molecules or even to ions within the cell's cytoplasm, which serve as the above-mentioned second messengers, whose diffusion enables a signal to propagate rapidly throughout the cell.

The number of second messengers appears at present to be surprisingly small. To put it another way, the internal signal pathways in cells are remarkably universal, and have been phylogenetically preserved over millions of years of evolution. Yet the known messengers are capable of regulating a vast variety of physiological and biochemical processes. The discovery of the identity of particular second-messenger substances is proving, therefore, to be of fundamental importance for understanding how cellular growth and function are regulated.

Several major signal pathways are now known, but two seem to be of primary importance. One employs cyclic nucleotides as second-messengers. These cyclic nucleotides activate a number of proteins inside the cell, which then cause a specific cellular response. The other major pathway employs a combination of second messengers that includes calcium ions as well as two substances whose origin is remarkable: inositol 1, 4, 5 trisphosphate ($IP_3$) and diacylglycerol (DG). These compounds are released from the plasma membrane itself, by enzymes that are activated by specific cellular membrane receptors. However, it should be noted that myoinositol in its non-phosphorylated form first enters an organism through the organism's diet, but can then be recycled as described hereinbelow.

$IP_3$ is formed by the following scheme. A receptor molecule on the surface of the cellular plasma membrane transmits information through the cellular plasma membrane and into the cell by means of a family of G proteins, which are cellular plasma membrane proteins that cannot be active unless they bind to guanosine triphosphate (GTP). The G proteins activate the so-called "amplifier" enzyme phospholipase C, which is on the inner surface of the cellular plasma membrane. Phospholipase C cleaves the cellular plasma membrane lipid phosphatidylinositol 4, 5-bisphosphate ($PIP_2$) into DG and $IP_3$. $IP_3$ is a water-soluble molecule and, therefore, upon being released from the inner surface of the cellular plasma membrane, it rapidly diffuses into the cytoplasm. $IP_3$ then releases calcium from internal compartments, which store high concentrations of calcium. The calcium released by $IP_3$ in turn activates a large number of intracellular enzymes that orchestrate a complex set of responses that allow the cell to adapt to the original signal triggering the receptor that caused the release of $IP_3$.

Quite fascinatingly, DG and $IP_3$ are recycled. DG is recycled by a series of chemical reactions which constitute one component of the lipid cycle. $IP_3$ is recycled by a series of reactions known as the phosphatidylinositol cycle. The two cycles converge at the point when inositol is chemically linked to DG. The DG-bound inositol is phosphorylated in a series of steps which ultimately results in the resynthesis of phosphatidylinositol bisphosphate.

In the first portion of the lipid cycle, DG is converted to phosphatidic acid, which in turn is converted to cytidine diphosphate diglyceride (CDP-DG), while in the first portion of the phosphatidylinositol cycle, $IP_3$ is dephosphorylated to ultimately form myoinositol. It is believed that such dephosphorylation occurs stepwise; $IP_3$ is converted to an inositol bearing only two phosphate groups ($IP_2$), followed by the loss of an additional phosphate, resulting in $IP_1$, which is then dephosphorylated to myo-inositol. Also, it has been shown that $IP_3$ can also undergo an additional phosphorylation, thereby being converted to inositol 1, 3, 4, 5 tetrakisphosphate ($IP_4$). This molecule is subsequently metabolized by successive removal of phosphate groups, as described above. It is believed that phosphatase enzymes catalyses each step of this process.

The lipid cycle and phosphatidylinositol cycle merge by the myo-inositol reacting with the CDP-DG to form phosphatidylinositol (PI) PI is phosphorylated to ultimately form $PIP_2$. It is believed that such phosphorylation occurs stepwise; PI is converted to phosphatidyl myo-inositol 4-phosphate (PIP), which is converted to $PIP_2$; the final step of both cycles. It is believed that a kinase enzyme catalyses each step of this process.

For an excellent review of $IP_3$, its role as a second messenger and the phosphatidylinositol cycle see Berridge, M., et al. *Inositol Triphosphate, a Novel Second Messenger in Cellular Signal Transduction*, Nature, 312, 315-321 (1984) and Berridge, M. *The Molecular Basis of Communication Within the Cell*, Scientific American, 142-152 (October 1985), and James W. Putney, Jr. (Ed.), *Phosphoinositide and Receptor Mechanisms*, Alan R. Liss, Inc., New York, N.Y. 1986.

3. SUMMARY OF THE INVENTION

The present invention relates to a method for detecting the phosphatidylinositol cycle-dependent calcium of a cell comprising:

a) contacting said cell with a compound represented by general formula I thereby permitting said compound to enter said cell:

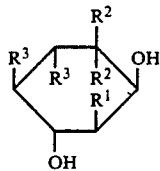

wherein:

$R^1$ is selected from the group consisting of $-OPO_3H_2$ and $-OPO_3^=$;

each $R^2$ is independently selected from the group consisting of $C_{1-8}$ linear or branched alkyl, $-F$, $-Cl$, $-Br$, $-I$, $-NH_2$, $-N_3$, $-NHOH$, $-NHNH_2$, $-CN$, $-NC$, $-SH$, $-SeH$, $-H$, and each $R^2$ can be joined to form $=NOH$, $=NNH_2$, $=O$ or $=S$; and each $R^3$ is independently selected from the group consisting $-OPO_3H_2$, $-OPO_3^=$ and $-OH$;

with the proviso that at least one of said $R^2$ is H except when:

(i) each $R^2$ is joined to form $=NOH$, $=NNH_2$, $=O$ or $=S$; and (ii) $R^2$ is $-F$, $-Cl$, $-Br$, or $-I$, then the other $R^2$ is $-F$, $-Cl$, $-Br$, $-I$, or H; and b) detecting the calcium of said cell.

The present invention also provides the compounds represented by general formula I.

DETAILED DESCRIPTION OF THE INVENTION

4 1 The Method of the Invention

The present invention relates to a method for detecting the phosphatidylinositol cycle-dependent calcium of a cell comprising:

a) contacting said cell with a compound represented by general formula I thereby permitting said compound to enter said cell:

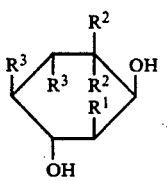

wherein:

$R^1$ is selected from the group consisting of $-OPO_3H_2$ and $-OPO_3^=$;

each $R^2$ is independently selected from the group consisting of $C_{1-8}$ linear or branched alkyl, $-F$, $-Cl$, $-Br$, $-I$, $-NH_2$, $-N_3$, $-NHOH$, $-NHNH_2$, $-CN$, $-NC$, $-SH$, $-SeH$, $-H$, and each $R^2$ can be joined to form $=NOH$, $=NNH_2$, $=O$ or $=S$; and each $R^3$ is independently selected from the group consisting of $-OPO_3H_2$, $-OPO_3^=$ and $-OH$; with the proviso that at least one of said $R^2$ is H except when:

(i) each $R^2$ is joined to form $=NOH$, $=NNH_2$, $=O$ or $=S$; and (ii) $R^2$ is $-F$, $-Cl$, $-Br$, or $-I$, then the other $R^2$ is $-F$, $-Cl$, $-Br$, $-I$, or H; and b) detecting the calcium of said cell.

It should be noted that general formula I, a Haworth projection, depicts the absolute stereochemistry.

The present invention also provides the compounds represented by general formula I. In a preferred embodiment, $R^1$ and each $R^3$ are $-OPO_3^=$. It is also preferred that general formula I have the myoinositol stereochemistry, i.e. the $R^2$ that is depicted in the Haworth projection below the plane of the cyclohexane ring be H.

Without being bound by theory, it is believed that the compounds of general formula I will mimic the action of $IP_3$. Thus, the compounds of general formula I will increase free intracellular calcium levels. This is because $IP_3$ mobilizes intracellular calcium and, some theorize, also permits extracellular calcium to enter the cell. However, unlike $IP_3$, the compounds of general formula I will not be converted to $IP_4$, thereby avoiding complications due to action of $IP_4$ on free intracellular calcium levels. Accordingly, the compounds of general formula I can be utilized to study $IP_3$ associated intracellular free calcium levels. Thus, one can detect cellular phosphatidylinositol cycle-dependent calcium changes. This is useful, for example, because one can detect the change in phosphatidylinositol cycle-dependent calcium caused by pharmacological agents that are designed to work through the phosphatidylinositol cycle.

The method of the invention is carried out by contacting the cell to be analyzed with a compound represented by general formula I thereby permitting the compound to enter the cell. Any type of cell can be utilized in the method. The choice of cell depends only on the cell system that one wants to study.

Prior to use, the compound represented by general formula I should be dissolved in an aqueous medium. The compound represented by general formula I is then contacted with the cell. It is essential that the contacting step results in the compound represented general formula I entering the cell. This contacting step can be carried out by any technique, for example, selective permeabilization, microinjection or caging. These three standard techniques are described in Gill, D. L. and Cheuh, S. H., *An intracellular (ATP+$Mg^{2+}$) dependent calcium pump within N1E-115 neuronal cell line*, J. Biol. Chem. 260:9289-9297 (1985); Oakes, S. G., Iaizzo, P. A., Richelson, E. and Powis, G., *Histamine-induced intracellular free $Ca^{2+}$, inositol phosphates and electrical changes in murine N1E-115 neuroblastoma cells*, Pharmacol. Exp. Ther. 247:114-121 (1988); and Walker, J. W., Somlyo, A. V., Goldman, Y. E., Somlyo, A. P. and Trentham, D. R., (1987) *Kinetics of smooth and skelatal muscle activation by laser pulse photolysis of caged inositol-1,4,5-trisphosphate*, Nature 327:249-252 (1987).

After the contacting step the calcium in the cell can be detected. Such detection can be carried out by any technique, for example, by utilizing $^{45}Ca^{+2}$, calcium sensitive microelectrodes, $Ca^{+2}$ sensitive fluorescent indicators, or $Ca^{+2}$ sensitive bioluminescent indicators. See Gill, D. L. and Cheun, S. H., *An intracellular ($ATP+Mg^{+2}$) dependent calcium pump within N1E-115 neuronal cell line*, J. Biol. Chem., 260:9289-9297 1985; Ammann, D., Meier, P. C. and Simon, W., *Design and use of calcium sensitive microelectrodes*, Detection and Measurement of Free $Ca^{2+}$ in Cells, (Eds. C. C. Ashley and A. K. Campbell), pp 117-129, Elsevier/North Holland, Amsterdam (1979); Grynkiewicz, G. Poenie, M. and Tsien, R. Y., *A new generation of $Ca^2$ + indicators with greatly improved flourescence properties*, J. Biol. Chem. 260:3340-3450; and Blinks, J. R., *Methods for monitoring $Ca^{2+}$ concentrations with photoproteins in living cardiac cells*, Methods for Studying heart Membranes, Volume II (Ed. N. S. Dhalla), pp. 237-264, CRC Press, Boca Raton (1984). These techniques also permit one to not only detect the calcium but also to measure the level of calcium.

In a preferred embodiment of the invention, one can measure the level of calcium in the cell prior to the contacting step. Thus, this permits one to detect and measure the change in the phosphatidlylinositol cycle-dependent calcium. Of course, this measurement of the level of calcium can be carried out by, for example, the techniques described hereinabove.

5. SYNTHESIS OF COMPOUNDS OF GENERAL FORMULA I

Methods of Synthesis of
D-3-Deoxy-3-Fluoro-myo-Inositol 1,4,5-Trisphosphate

A detailed description of the method of synthesis of the title compound follows. Formulae for all the structures of the compounds named in the detailed description can be found in Scheme 1.

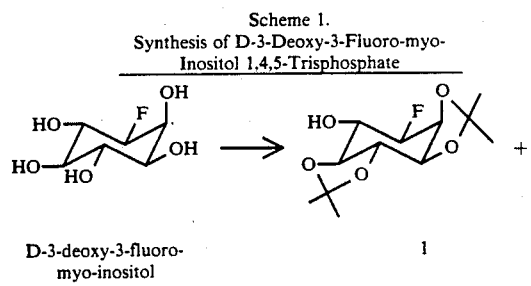

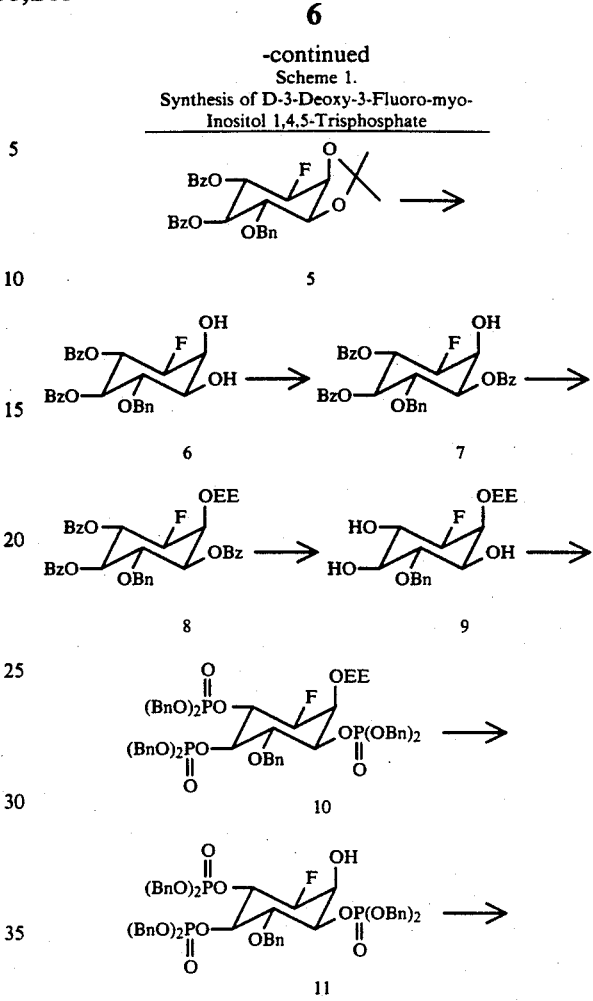

Bn = —CH$_2$Ph
Bz = —$\overset{O}{\underset{\|}{C}}$Ph
EE = —CH(CH$_3$)OCH$_2$CH$_3$ Preparation of
1,2:5,6-di-O-cyclohexylidene-3-deoxy-3-fluoro-myo-inositol (1) and
1,2:4,5-di-O-cyclohexylidene-3-deoxy-3-fluoro-myo-inositol (2)

To a stirred mixture of 3-deoxy-3-fluoro-myo-inositol (1,82 g, 10.0 mmol) and camphorsulfonic acid (50 mg) in DMF at 55° C. under argon was addes neat 2-methoxypropene (3.83 mL, 40 mmol). The mixture was stirred for 4 h at 80° C. and cooled. Triethylamine (4 mL) was added and the solvent was distilled off in vacuo. The light brown residue was chromatographed over silica gel using 40–50% ethyl acetate in hexane to furnish a 2.3:1 ratio of the diacetonides 1 and 2; yield =2.1 g, 82.6%.

1. $[\alpha]_D^{23}$ —52° (c=5 mg/mL, CHCl$_3$): mp 154°–156° C.; IR (Nujol) 3520, 2990, 1373, 1240, 1057, 868 cm$^{-1}$;

$^1$H NMR δ 4.64 (ddd, J=46.4, 3.3, 3.3 Hz, H-3), 4.95 (ddd, J=22.6, 6.6, 3.3 Hz, H-2), 4.41 (ddd, J=6.6, 6.6 Hz, H-1), 4.27 (ddd, J=17.3, 8.5, 3.4, 3.3 Hz, H-4), 3.98 (ddd, J=10.7, 6.6, 3.3 Hz, H-6), 3.47 (dd, J=10.7, 8.5 Hz, H-5) 2.44 (d, J=3.4 Hz, OH), 1.53 (s, 3 H), 1.45 (s, 6H, 1.39 (s, 3 H); $^{13}$C NMR (75 MHz, CDCl$_3$) δ112.62 (s), 110.31 (s), 88.25 (d,J=189 Hz), 81.41 (s), 76.81, 75.81, 75.19 (d, J=15 Hz), 74.72 (d, J =18.7 Hz), 73.64 (s), 27.48 (s), 26.30 (s), 26.29 (s), 25.37 (s); mass spectrum, (EI) m/z 247 (M+−CH$_3$), 207, 187, 101, 59; HRMS calcd for M+−CH$_3$ 247.0982. found 247.0982.

2. [α]$_D^{23}$+7.2° (c=5 mg/mL, CHCl$_3$); mp 206°–207° C.; IR (KBr disk) 3550, 2980, 1773, 1238, 1050, 867 ch$^{-1}$; $^1$H NMR (300 MHz, CDCl$_3$) δ 4.86 (ddd, J=48.8, 10.1, 4.6 Hz, H-3), 4.78 (ddd, J=4.6, 2.3, 2.3 Hz, H-2), 4.14 (dd, J=10.1, 10.1 Hz, H-4), 4.08 (dd, J=6.5, 2.3 Hz, H-1), 3.94 (ddd, J=10.6, 6.5, 3.0 Hz, H-6), 3.33 (ddd, J=10.6, 10.1 1.5 Hz, H-5), 2.63 (d, J=3.0 Hz, OH), 1.57 (s, 3H), 1.49 (s, 3 H), 1.47 (s, 3 H), 1.40 (s, 3H); $^{13}$C NMR (75 MHz; CDCl$_3$) δ 112.04 (s), 110.79 (s), 93.64 (d, J=187 Hz), 77.78 (s), 76.89 (s), 75.97 (s), 73.91 (d, J=18 Hz), 71.0 (d, J=2.5 Hz), 26.45 (s, 2 C),, 26.15 (s), 24.79 (s); mass spectrum, (EI) m/z 262 (M+), 247, 129, 101, 59; HRMS calcd for M+-15 247.0982, found 247.0982.

Preparation of 6-O-benyl-1,2:4,5-di-O-cyclohexylidene-3-deoxy-3-fluoro-myo-inositol (3)

To a stirred suspension of sodium hydride (0.5 g of 50% oil dispersion) in 20 mL of dry THF under argon, was added a solution of the diacetonide 2 (1.7 g, 6.5 mmol) in THF via cannula. After stirring for 15 min, a solution of benzyl bromide (1.24 mL, 10.41 mmol) in THF was added via cannula. The mixture was stirred overnight and quenched by adding water and ether. The aqueous phase was extracted with ether three times. The ether extracts were combined and washed with water and saturated sodium chloride and dried (MgSO$_4$). After concentration in vacuo, a glassy solid was obtained which was chromatographed on silica gel (20% ethyl acetate in hexane) to yield 2.19 g (96%) of the diacetonide 3:

[α]$_D^{23}$ −79.7° (c=7.9 mg/mL, CHCl$_3$); mp 135°–138° C.; IR (Nujol) 2990, 2950, 1575, 1375, 1220, 1080 cm$^{-1}$; $^1$H MHz, CDCl$_3$) δ7.40-7.25 (m, 5 H), 4.81 (ddd, J=49, 10.2, 4.5 Hz, H-3), 4.55 (ddd, J=4.6, 2.4, 2.4 Hz, H-2), 4.20 (dd, J=5.8, 5.8 Hz, H-1), 4.09 (dt, J=19.4, 9.7, 9.7, H-4), 3.70 (dd, J=10.8, 6.5, H-5), 3.40 (ddd, J=10.8, 10.8, 1.5 Hz, H-6), 1.49 (s, 3 H), 1.46 (s, 3 H), 1.39 (s, 3 H), 1.37 (s, 3 H); $^{13}$C NMR (75 Hz, CDCl$_3$) δ137.5 (s), 127.73 (s, 2 C), 127.44 (s, 2 C), 127.08 (s), 112.39 (s), 110.09 (s), 88.22 (d, J=188 Hz), 80.81 (s), 79.20 (s), 77.25 (s), 75.27 (d, J=15 Hz), 74.62 (d, J=18 Hz), 71.50 (s), 27.20 (s), 26.35 (s), 26.34 (s), 25.39 (s); mass spectrum, (EI) m/z 352 (M+), 337 (M+-CH3), 294, 246, 203, 145, 91, 59; HRMS calcd for C$_{19}$H$_{25}$FO$_5$ 352.1696, found 352.1686.

Preparation of 6-O-benzyl-1,2-O-cyclohexylidene-3-deoxy-3-flouro-myo-inositol (4)

A solution of the dicetonide 3 (2.0 g, 5. mmol) and four drops of acetyl chloride in 100 mL of methanol was stirred at room temperature for 4 h or until the TLC showed completion of reaction. One mL of triethylamine was added and the volatiles were evaporated under reduced pressure and the pale yellow residue was chromatographed (silica gel) with 80% ethyl acetate in hexane to furnish 1.53 g (86%) of the monoacetonide 4 as a solid.

[α]$_D^{23}$ −30.4° (c=4.5 mg/mL, MeOH); mp 141°–144° C.; IR (Nulol) 3566, 3250, 1366, 1105, 870 cm$^{-1}$; $^1$H NMR (300 MHz, CDCl$_3$) δ6 4.93 (d, J=11.5 Hz, —CH$_2$—), 4.66 (d, J=1.5 Hz, —CH$_2$—), 4.60 (ddd, J=47, 8.6, 4.7 Hz, H-3), 4.52 (m, H-2), 4.24 (dd, J=6.6, 5.8, H-1), 4.08 (m, H-4), 3.59 (dd, J=9.5 6.6, H-6), 3.41 (ddd, J=9.5, 9.5, 2.4 Hz, H-5), 2.79 (m, 2 OH), 1.52 (s, 3 H), 1.40 Is, 3 H); $^{13}$C NMR (75 MHz, CDCl$_3$) δ 137.75 (s), 128.50 (s), 128.08 (s), 127.99 (s), 10.8 (s), 90.3 (d, J=184 HZ), 81.33 (s), 79.97 (s), 74.10 (d, J=15.7 Hz), 73.25, 72.50 (d, J=9.8 Hz), 70.82 (d, J=21 Hz), 27.67 (s), 25.84 (s); mass spectrum, (EI) m/z 312 (M+), 297, 254, 173, 107, 91; HRMS calcd for C$_{16}$H$_{21}$FO$_5$ 312.1373, found 312.1373.

Preparation of 1,2-O-oyclohexylidene-4,5-di-0-benzoyl-6-O-benzyl-3-deoxy-3-fluoro-myo-inositol (5)

Benzoyl chloride (1.9 mL, 16.0 mmol) was added via syringe under argon, to a stirred solution of the 5 diol 4 (2.0 g, 6.4 mmol) in 60 mL of pyridine at room temperature. After stirring for 12 h pryidine was distilled off in vacuo and the light yellow residue was directly chromatographed on silica gel using 20% ethyl acetate in hexane to afford 3.06 g (92%) of the dibenzoate 5 as a foam.

[α]$_D^{23}$ −52.24° (c=12.25 mg/mL, CHCl$_3$); mp below 70° C.; IR (Nujol) 1728, 1425, 1275, 1100, 1070 cm$^{-1}$; $^1$H NMR (CDCl$_3$, 300 MHz) δ 8.00 (d, J=7.7 Hz, 4 H), 7.51 (m, 2 H), 7.40 (m, 4 H), 7.25 (m, 5 H), 5.98 (dd, J=16.8, 9.3, H-4), 5.49 (dd, J=6.8, 6.8 Hz, H-2), 5.06 (ddd, J=47, 9.3, 3.7 Hz, H-3), 4.85 (bs, —CH$_2$—), 4.73 (m, H-2), 4.5 (dd, J=6.6 Hz, H-6), 3.98 (dd, J=6.8, 6 Hz, H-1), 1.63 (s, 3 H), 1.41 (s, 3 H); $^{13}$C NMR (CDCl$_3$, 75 MHz) δ 165.77 (s), 165.42 (s), 137.34 (s), 133.26 (s), 129.84 (s), 129.40 (s), 129.27 (s), 128.35 (s), 127.96 (s), 127.86 (s), 110.98 (s), 87.60 (d, J=187 Hz), 77.51 (d, J=14.2 Hz), 76.69 (d, J=31.2 Hz), 73.44 (m, 2 C), 72.76 (s), 70.71 (d, J=21.8 Hz), 26.79 (s), 24.89 (s); mass spectrum, (EI) m/z 505 (M+−15), 415, 309, 292, 277, 105, 91; HRMS calcd for C$_{29}$H$_{26}$FO$_7$ 505.1663, found 505.1663.

Preparation of 4,5-di-O-benzoyl-6)-benzyl-3deoxy-3-fluore-myo-inositol (6)

The dibenzoate 5 (3.2 g, 6.1 mmol) was dissolved in 100 mL of MeOH containing 20 drops of conc. HCl. The mixture was let stand at room temperature for 6 h. Triethylamine (4 mL) was added and the volatiles were stripped off under vacuum. The resulting residue was directly chromatrographed on silica gel using 40% ethyl acetate in hexane to yield 2.7 g (92%) of the diol 6 as a white solid.

[α]$_D^{23}$ −65.8. (c=4.6 mg/mL, CHCl$_3$); mp 64°–66° C.; IR (thin film) 3500, 1728, 1718, 1450, 1277, 1105, cm$^{-1}$; $^1$H NMR (CDCl$_3$, 300 MHz) δ7.90 (m, 4 H), 7.49 (m, 2 H), 7.38 (m, 4H), 7.19 (m, 5 H), 6.06 (dd, J=21, 10 Hz, H-4), 5.55 (dd, J=10, 10 Hz, H-5), 4.72 (ddd, J=47.7, 9.7, 2.8 Hz, H-3), 4.69 (AB q, J=11.2 Hz, —CH$_2$—) 4.48 (m, H-2), 4.13 (dd, J=9.5, 9.5 Hz, H-6), 3.82 (m, H-1), 2.77 (bs, OH), 2.59 (d, J=5 Hz, OH); $^{13}$C NMR (CDCl$_3$, 75 MHz) δ165.71 (s), 137.51 (s), 133.25 (s), 133.20 (s), 129.75 (s), 129.12 (s), 128.39 (s), 128.30 (s), 128.05 (s), 127.92 (s), 89 9 (d, J=187 Hz), 79.10 (s), 75.31

(s), 71.95 (d, J=12.4 Hz), 70.85 (s), 70.60 (d, J=10.1 Hz), 70.15 (d, J=17.3 Hz); mass spectrum, (EI) mz/ 480, 375, 269, 252, 105, 91, 77; HRMS calcd for $C_{27}H_{25}FO_7$ 480.15843, found 480.15843.

Preparation of 1,4,5-tri-O-benzoyl-6-O-benzyl-3-deoxy-3-fluoro-myo-inositol (7)

A mixture of the diol 6 (0.63 g, 1.32 mmol), 169 mL of benzoyl chloride, and a few crystals of DMAP in 20 mL of dry pyridine under argon was stirred for 8 h at 0° C. Pyridine was distilled off under vaccum, and the yellow residue was directly purified by silica gel chromatography using a gradient elution (40%–60% ethyl acetate in hexane) to give 0.692 g (89.3%) of the tribenzoate 7 as a white solid.

$[\alpha]_D^{23}$ −52.6° (c=3.65 mg/mL, CHCl$_3$); mp 180°–183° C.; IR(Nujol) 3500, 1728, 1452, 1315, 1271, 1107, 1028 cm$^{-1}$; $^1$H NMR (CDCl$_3$, 300 MHz) δ8.09 (d, J=7.3 Hz, 2 H), 7.93 (t, J=8.7 Hz, 4 H), 7.61 (t,J=7.5 Hz), 7.48 (m, 4 H), 7.36 (t, J=7.7 Hz, 4 H), 7.01 (m, 5 H), 6.13 (dd, J=21, 10 Hz, H-4), 5.66 (dd, J=9.8, 9.8 Hz, H-5), 5.29 (bd-, J=9.8 Hz, H-1), 4.83 (ddd, J=48, 9.5, 2.5 Hz, H-3), 4.72 (m, H-2), 4.65 (AB q, J=11.2 Hz, —CH$_2$—), 4.53 (dd, J=9.8, 9.8 Hz, H-6), 2.77 (—OH); $^{13}$C NMR (CDCl$_3$, 75 MHz) δ165.61(s), 133.51(s), 165.42 (s), 133.18(s), 129.81 (s), 129.74 (s), 129.28 (s), 129.15 (s), 129.08 (s), 128.54 (s), 128.31 (s), 128.11 (s), 127.89 (s), 127.63 (s), 89.74 (d, J=185 Hz), 75.35 (s), 72.62 (d, J=11.2 Hz), 71.72 (d, J=12.8 Hz), 70.50 (d, J=20 Hz), 68.7 (d, J=19.5 Hz); mass spectrum, (EI) m/z 584 (M+), 566, 479, 176, 106, 91; HRMS calcd for $C_{34}H_{29}FO_8$ 584.1675, found 584.1675.

Preparation of 1,4,5-tri-O-benzoyl-6-O-benzyl-3-deoxy-3-fluoro-myo-inositol, 2-ethoxyethyl ether (8)

A homogenous solution of the tribenzoate 7 (0.692 g, 1.18 mmol), ethyl vinyl ether (140 μL, 1.56 mmol) and a catalytic amount of pyridium p-toluenesulfonate was stirred at room temperature in CH$_2$Cl$_2$ for 12 h. Solvent was removed under reduced pressure and the resulting residue was chromatographed on silica gel to afford 0.67 g (86.2%) of the protected tribenzoate 8 as a foam.

$[\alpha]_D^{23}$ −45° (c=1.8 mg/mL, CHCl$_3$); mp 65°–68° C.; IR (thin film) 1728, 1452, 1315, 1269, 1176, 1095, 960 cm$^{-1}$; $^1$H NMR (CDCl$_3$, 300 MHz) δ8.05 (m, 2 H), 7.61 (m, 1 H), 7.50 (m, 4 H), 7.39 (m, 4 H), 7.10 (m, 5 H), 6.2–6.0 (m, 1 H), 5.63 (t, J=9.8 Hz, 1 H), 5.22 (m, 1 H), 4.90-4.40 (m, 5 H), 3.91 (m, 5 H), 3.65-3.51 M, 1.5 H), 3.32 (m, 1 H), 1.47 (d, J=5.2 Hz, 1.5 H), I.32 (d, J=5 Hz, 1.5 H), 1.19 (t, J=7 Hz, 1.5 H), 0.80 (t, J=7 Hz, 1.5 H); mass spectrum, (EI) m/z 656 (M ), 585, 408,372,208,190,91; HRMS calcd for C 656.7113, found 656.7113.

Preparation of 6-O-benzyl-3-deoxy-3-fluoro-myo-inositol, 2-ethoxyethyl ether (9)

Anhydrous potassium carbonate (2.0 g. 14.4 mmol) was added to a stirred solution of the tribenzoate 8 (0.67 g, 1.02 mmol) in 50 mL of anhydrous methanol. The suspension was stirred overnight at room temperature and concentrated at reduced pressure. Water and NaCl were added and the aqueous phase was extracted with ethyl acetate(3×). After drying (MgSO$_4$), and concentration, the residue was purified by silica gel chromatography (70% ethyl acetate in hexane) to leave 0.29 g (835) of the triol as a wax.

$[\alpha]_D^{23}$ −11.16° (c=28 mg/mL, CHCl$_3$); IR (thin film) 3475, 1475, 1375, 1105, 1050 cm$^{-1}$; $^1$H NMR (CDCL$_3$, 300 MHZ) 6 740-7.24 (m, 5 H), 5.06 (d, J=11.5 Hz, 0.5 H), 4.86 (m, 0.5 H), 4.81 (AB q, J=11.2 Hz, I H), 4.69 (d, J=11.2 Hz, 0.5 H), 4.62 (m, 0.5 H), 4.40 (m, 0.5 H), 4.21 (m, 1 H), 4.18-3.95 (m, 1.5 H), 3.82 (m, 1 H), 3.62-4.47 (m, 3 H), 3.41 (m, 0.5 H), 3.31 (m, 0.5 H), 2.8 (bs, 3 OH), 1.38 (d, J=5 Hz, 1.5 H), 1.32 (d, J=5 Hz, 1.5 H), 1.22 (t, J=7 Hz, 1.5 H), 1.21 (t, J=7 Hz, 1.5 H); mass spectrum (EI) m/z 344 (M ), 326, 308, 244, 189, 91; HRMS calcd for $C_{17}H_{25}FO_6$ 344.2941, found 344.2941.

Preparation of 6-O-benzyl-3-deoxy-3-fluoro-myo-inositol 1,4,5-trisphosphate, hexabenzyl ester (11)

Sodium hydride (0.179 g, 3.7 mmol, 50% suspension in mineral oil) was added under argon to a stirred solution of the triol (o.117 g, 0.34 mmol) and tetrabenzyl pyrophosphate (1.10 g, 2.04 mmol) in anhydrous DMF at 0° C. After stirring the mixture between 0°–5° C. for 9 h, the DMF was distilled off at 0.5 mm Hg pressure using a cold (25° C.) water bath. Methylene chloride (50 mL) was added, and the heterogeneous suspension was stirred for 15 min and filtered through Celite. The fitrate was concentrated in vacuo. The white residue was directly chromatographed on silica gel (60% ethyl acetate in hexane) to yield 0.372 g (95%) of 10 as a colorless oil. (FAB) 1125 (M+1), 1079, 1053, 963, 873, 419, 391, 181, 149, 129.

A few crystals of p-toluenesulfonic acid were added to a stirred solution of 10 (0.36 g, 0.32 mmol) in 10 mL of absolute methanol for 3h. Methanol was stripped off under rotary evaporation, and the resulting residue was rapidly filtered through silica gel with 80% ethyl acetate in hexane to afford 0.28 g (78.2%) of the 11 as a wax.

$[\alpha]_D^{23}$ −6.8° (c =30 mg/mL, CHCl$_3$); IR (thin film) 3300, 1496, 1456, 1381, 1271, 1155, 1016 cm$^{-1}$; $^1$H NMR (CDCl$_3$, 300 MHz) δ 7.40-6.90 (m, 35 H), 5.15-4.68 (m, 14 H), 4.63 (dd, J=11.7 Hz, 9 Hz, 1 H), 4.50-4.37 (m, 2.5 H, includes a part of the signal for C-3 proton), 4.21 (dd, J=9.5, 2.3 Hz, 0.5 H, a part of C-3), 4.15 (bt, J=8.4 Hz, 1 H), 3.9 (t, J=9.4 Hz, 1 H), 2,99 (bs, OH); $^{31}$P NMR (CDCl$_3$, 201 MHz, 85% phosphoric acid standard, H-decoupled) δ−4.34, −4.79, −5.00 ppm; $^{19}$F NMR (470 MHz, CDCl$_3$, CFCl$_3$ as standard, $^1$H-coupled) φ204.57 (dt, J=47, 9.9 Hz); (FAB) 1053 (M++1), 963, 873, 783, 181, 136.

Preparation of 3-deoxy-3-fluoro-myo-inositol-1,4,5trisphosphate, hexasodium salt (12)

A 25 mL round-bottomed flask was charged with 11 (0.28 g, 0.266 mmol) and 15 mL of absolute ethanol. Platinum oxide (20 mg) was added, and the contents were purged with hydrogen and stirred in the same atmosphere (using a balloon) at room temperature overnight. Following filtration over Celite and concentration in vacuo, the oily residue was dissolved in 2 mL of distilled water and treated with 6 equiv. of 1N NaOH and concentrated to a small (1 mL) volume Methanol (5 mL) was added, and the white precipitate formed was filtered and washed several times with methanol and dried to afford 0.12 g (79%) of 12 as a white powder.

$[\alpha]_D^{23}$ −8.5° (c=3.75 mg/mL, $H_2O$); $^1H$ NMR ($D_2O$, 500 MHz, pH=9, $D_2O$ peak set at 4.78 ppm) δ4.56 (m, 1.5 H, includes a part of the signal for C-3 proton), 4.50–4.36 (m, 1.5 H, includes a part of the signal for C-3 proton), 3.920–3.78 (m, 3 H); $^{31}P$ NMR ($D_2O$, pH=9, 201 MHz, H-coupled) δ4.63 (bs), 3.38 (bs), 319(s); $^{19}F$ NMR ($D_2O$, pH=9, 470 MHz, H-coupled) Φ198.02 (bd, J~44 Hz).

By employing one of the other halogen (Br, Cl or I) substituted inositols in place of D-3-deoxy-3-fluoro-myo-inositol in the above reaction sequence, any of the other 3-halogen substituted inositol 1,4,5-trisphosphates can be prepared. To prepare the 1,4bisphosphate, 1,5-bisphosphate or 1-phosphate analogues, protection of either the 4-hydroxyl group or the 5-hydroxyl group, or both hydroxyl groups by benzylation is required. After phosphorylation of any remaining free hydroxyl groups as in the conversion of 9 to 10 in the above scheme, all benzyl groups are removed by hydrogenolysis and any remaining protecting groups cleaved under standard conditions to provide the desired monophosphate or bisphosphate analogues.

To prepare the inositol 1,4,5-trisphosphate analogues bearing an amino or azido group at the D-3 position, the following sequence of synthetic operations can be employed (Scheme 2). In view of the extensive experimental description provided for the synthesis of D-3-deoxy-3-fluoro-myo-inositol 1,4,5-trisphosphate only the chemical reaction sequence is drawn out for the amine and azide bearing inositol phosphates. The methods-used involve standard synthetic operations. By starting from other substituted inositols (e.g., —SH, CN,—N=C, etc.) and following similar reactions schemes, any of the other inositol phosphates of the present invention can be prepared readily.

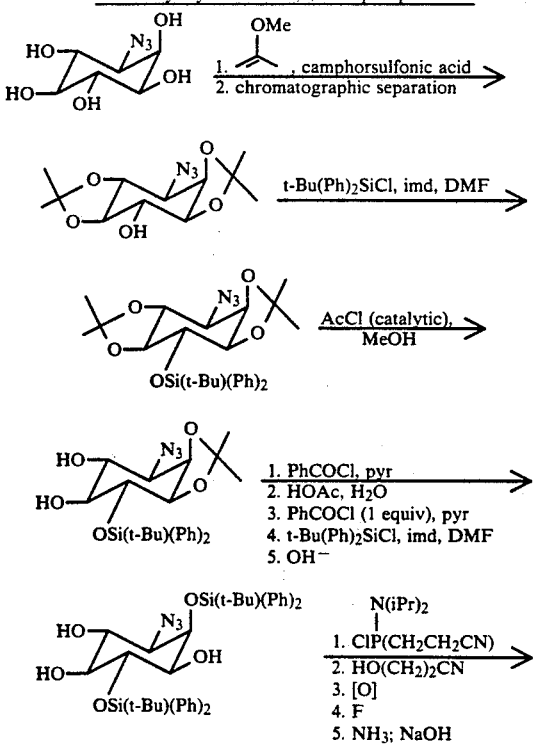

Scheme 2.
Synthesis of D-3-Amino and D-3-Azido-3-Deoxy-myo-Inositol 1,4,5-Trisphosphate.

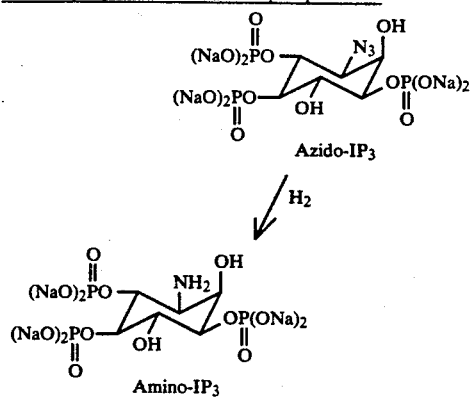

EXAMPLE

To investigate the effect of 3-F $IP_3$ on $Ca^{2+}$ release, Swiss 3T3 cells were permeabilized with medium containing 0.005% saponin as described in Seewald et al., Cancer Communications, 1,151 (1989). After washing, the cells were incubated in medium containing 1 mM ATP, 3% polyethylene glycol, 50 uM $^{45}Ca^{2+}$ (160 uCi/mmol) and EGTA to buffer the free $Ca^{2+}$ to a concentration of $10^{-7}$ M. The cells were collected on glass microfiber filters and washed with buffer containing 1 mM $LaCl_3$ prior to liquid scintillation counting. Preliminary studies showed that $^{45}Ca^{2+}$ uptake by Swiss 3T3 cells reached a plateau by 6 min. $IP_3$ (Molecular Probes, Irvine, CA) or 3-F $IP_3$ was added at 6.25 min, and the $^{45}Ca^{2+}$ remaining in the cells was measured at 7 min. All determinations were conducted in quintuplet. $^{45}Ca^{2+}$ release is expressed as the percent release measured at 7 min compared to the 6 min value for each pair of determinations and corrected for $^{45}Ca^{2+}$ release in the absence of added agent.

As can be seen from the dose response curve presented in Table I, 3-F $IP_3$ acts as a full agonist in releasing $^{45}Ca^{2+}$ from the 3T3 cells. The unnatural fluorinated $IP_3$ analogue is equipotent to natural $IP_3$. Dextran sulfate, a potent blocker of the release of $Ca^{2+}$ $IP_3$ also blocked the release of $Ca^{2+}$ induced by 3-F $IP_3$ (data not shown). From the studies it is apparent that interaction of $IP_3$ with its receptor on the edoplasmic reticulum does not require the 3-hydroxyl group either for recognition or for functional activity.

The findings obtained from this study are significant, for they reveal an important new tool for the study of PI-based cell signalling: 3-F $IP_3$ exhibits the same agonist effects as $IP_3$ on $Ca^{2+}$ release, but its role is not further complicated by a possible simulatenous action of 3kinase(s) to produce $IP_4$. This compound is thus to be recommended in place of $IP_3$ in studying intracellular $Ca^{2+}$ release.

TABLE I

| Release of $^{45}Ca^{2+}$ from non-mitochondrial stores of saponin-permeabilized Swiss 3T3 cells by 3-F $IP_3$ and $IP_3$. | | | | |
|---|---|---|---|---|
| Concentration (μM) | | | | |
| 0 | 0.5 | 1.0 | 3.0 | 10.0 |
| $^{45}Ca^{2+}$ release % | | | | |
| $IP_3$  0 | 16.1 ∓ 5.2 | 23.4 ∓ 4.4 | 31.3 ∓ 4.6 | 38.2 ∓ 3.7 |

TABLE I-continued

Release of $^{45}Ca^{2+}$ from non-mitochondrial stores of saponin-permeabilized Swiss 3T3 cells by 3-F IP$_3$ and IP$_3$.

| | Concentration (μM) | | | | |
|---|---|---|---|---|---|
| | 0 | 0.5 | 1.0 | 3.0 | 10.0 |
| 3-FIP$_3$ | 0 | 12.8 ∓ 5.9 | 20.1 ∓ 4.3 | 29.4 ∓ 5.9 | 39.2 ∓ 2.1 |

Note: All determinations were conducted in quintuplet
Values are mean ∓ S.D. and are the release at 7 min. expressed as a percent of the $^{45}Ca^{2+}$ in the cell at 6 min. (equilibrium value) corrected for $^{45}Ca^{2+}$ release in the abscence of added agents. The agents were added at the concentrations shown at 6.25 min.

What is claimed is:

1. A compound represented by the general formula I:

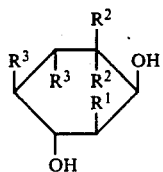

wherein:
  $R^1$ is selected from the group consisting of —OP)$_3$H$_2$ and —OPO$_3$=;
  each $R^2$ is independently selected from the group consisting of C$_{1-8}$ linear or branched alkyl, —F, —Cl, —Br, —I, NH$_2$, —N$_3$, —NHOH, —NHNH$_2$, —CN, —NC, —SH, —SeH, —H, and each $R^2$ can be joined to form =NOH, =NNH$_2$,
  each $R^3$ is independently selected from the group consisting of —OPO$_3$H$_2$, —OPO$_3$= and —OH;
  with the proviso that at least one of said $R^2$ is H except when:
    (i) each $R^2$ is joined to form =NOH, =NNH$_2$, =O or =S; and
    (ii) $R^2$ is —F, —Cl, —Br, or —I, then the other $R^2$ is —F, —Cl, —Br, —I, or H.

2. The compound of claim 1 wherein $R^1$ and each $R^3$ are —OPO$_3^{50}$.

3. The compound of claim 1 of the myo-inositol stereochemistry.

4. The compound of claim 1 wherein at least one of said $R^2$ is selected from the group consisting of —F, —Cl, —Br, and —I.

5. The compound of claim 1 wherein at least one of said $R^2$ is —F.

* * * * *